US010571252B2

(12) United States Patent
Angot et al.

(10) Patent No.: US 10,571,252 B2
(45) Date of Patent: Feb. 25, 2020

(54) SURFACE TOPOGRAPHY OPTICAL MEASURING SYSTEM AND SURFACE TOPOGRAPHY OPTICAL MEASURING METHOD

(71) Applicant: Industrial Technology Research Institute, Hsinchu (TW)

(72) Inventors: Ludovic Angot, Hsinchu (TW); Yueh-Yi Lai, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 16/036,952

(22) Filed: Jul. 17, 2018

(65) Prior Publication Data
US 2020/0025555 A1    Jan. 23, 2020

(51) Int. Cl.
| | |
|---|---|
| *G01B 11/22* | (2006.01) |
| *G01N 21/88* | (2006.01) |
| *G01B 11/14* | (2006.01) |
| *G01B 11/02* | (2006.01) |

(52) U.S. Cl.
CPC .............. *G01B 11/22* (2013.01); *G01B 11/02* (2013.01); *G01B 11/14* (2013.01); *G01N 21/8806* (2013.01)

(58) Field of Classification Search
CPC ......... G01B 11/22; G01B 11/02; G01B 11/14; G01N 21/8806
USPC .................................................. 356/601–624
See application file for complete search history.

(56) References Cited

U.S. PATENT DOCUMENTS

| | | |
|---|---|---|
| 6,823,724 B1 | 11/2004 | Kobayashi et al. |
| 7,668,364 B2 | 2/2010 | Lizotte et al. |
| 8,069,008 B2 | 11/2011 | Kusunose |
| 9,606,269 B2 | 3/2017 | Kumar et al. |
| 2010/0284027 A1 | 11/2010 | Scheiner |

(Continued)

FOREIGN PATENT DOCUMENTS

| | | |
|---|---|---|
| CN | 105117074 | 12/2015 |
| CN | 107764204 | 3/2018 |
| TW | I487898 | 6/2015 |

(Continued)

OTHER PUBLICATIONS

"Office Action of Taiwan Counterpart Application," dated May 2, 2019, p. 1-p. 3.

*Primary Examiner* — Tri T Ton
(74) *Attorney, Agent, or Firm* — JCIPRNET

(57) ABSTRACT

A surface topography optical measuring system including image capture modules, a control module and a computation module is provided. Each image capture module includes an electronically controlled focal length tunable lens, an optical assembly and an image sensor, wherein the image capture modules respectively capture images at different heights between a lowest and a highest surfaces of an object. The control module is coupled to the image capture modules to independently control the image capture modules. The computation module is coupled to the control module and the image sensor of each image capture module, wherein the computation module perform calibration of the surface topography optical measuring system and assesses in-focused pixels in the captured images to measure a height difference between a highest and a lowest surfaces of the object or between any surfaces of interest of the object. A surface topography optical measuring method is also provided.

15 Claims, 8 Drawing Sheets

(56) References Cited

U.S. PATENT DOCUMENTS

2011/0184694 A1 7/2011 Grimberg et al.
2014/0168660 A1 6/2014 Yan et al.

FOREIGN PATENT DOCUMENTS

| TW | I489101 | 6/2015 |
| TW | I516743 | 1/2016 |
| TW | I558976 | 11/2016 |
| TW | I568989 | 2/2017 |
| TW | 201718147 | 6/2017 |

SURFACE TOPOGRAPHY OPTICAL MEASURING SYSTEM AND SURFACE TOPOGRAPHY OPTICAL MEASURING METHOD

BACKGROUND

Field of the Disclosure

The disclosure relates to a surface topography optical measuring system and a surface topography optical measuring method.

Description of Related Art

In the field of Automatic Optical Inspection (AOI), non-contact three-dimensional measurement occupies an important position. Examples of non-contact three-dimensional measurement technologies are chromatic confocal microscopy, white light interferometry and conoscopic holography. While these technologies provide accurate and precise depth measurements, they do so for single points and therefore do not offer any two dimensional (2D) image of the surface under inspection: if a 3D measurement is required, a time consuming two dimensional scanning of the surface has to be undertaken, and no spectral information of the surface, such as the color of the surface, is provided. There exists three-dimensional measurement technologies based on focus (focus variation, depth from focus, depth from defocus) which provide 2D images of the surface of the object and spectral information of the surface. However current implementation of focus based approaches are limited by their narrow field of view (FOV) and the mechanical motion range. In particular, measuring the depth of blind holes or similar structure having a diameter much larger than the system's field of view requires a scanning along one of the direction perpendicular to the optical axis of the system; and if, in addition, the depth or height of the object to inspect is large, then another long range motion along the Z axis of the system is required. The conventional approach therefore is time consuming and can be limited by the range of the system. It is an object of the present invention to provide a fast yet accurate three dimensional measurement of structures while providing surface topology as well as 2D color images of the object under inspection.

SUMMARY

The disclosure provides a surface topography optical measuring system and a surface topography optical measuring method capable of offering 2D images of the surfaces under inspection and obtaining the surface topography of the object.

A surface topography optical measuring system of the disclosure includes a plurality of image capture modules, a control module and a computation module. Each of the plurality of image capture modules includes an electronically controlled focal length tunable lens, an optical assembly and an image sensor, wherein the plurality of image capture modules respectively capture images at different heights between a lowest and a highest surface of an object. Said lowest and highest surfaces of the object define the surfaces of interest, that is between which some physical quantities such as, but not limited to, height, lateral dimensions, reflectance, are to be measured. Said lowest and highest surfaces are not necessarily the lowest and highest surfaces of the object, but can represent a local lowest and a local highest surface. The control module is coupled to the plurality of image capture modules to independently control the plurality of image capture modules. The computation module is coupled to the control module and the image sensor of each of the plurality of image capture modules, wherein the computation module performs calibration of the surface topography optical measuring system and assesses in-focused pixels in the captured images to measure a height difference between a highest and a lowest surfaces of the object or between any surfaces of interest of the object.

A surface topography optical measuring method of the disclosure uses the surface topography optical measuring system described above. The surface topography optical measuring method of the disclosure includes steps as follows. Obtaining a relationship between an electrical parameter and a focus distance of each of the plurality of image capture modules. Performing a calibration on the plurality of image capture modules so that a predetermined height difference is obtained between focus distances of the plurality of image capture modules when the electronically controlled focal length tunable lens of each of the plurality of image capture modules is in an idle state, that is when each of the plurality of image capture modules is focused at its default focus distance, that is, either without any electrical control parameter applied to the electronically controlled focal length tunable lens or when a reference electrical control parameter is applied to the electronically controlled focal length tunable lens. Performing local depth measurements between a highest and a lowest surfaces of an object respectively by the plurality of calibrated image capture modules, so that images within focusing ranges of each of the plurality of calibrated image capture modules and containing in-focus pixels are captured. Obtaining a height difference between a highest and a lowest surfaces of the object or between any surfaces of interest of the object based on the captured images and the predetermined height difference.

In order to make the aforementioned and other features and advantages of the invention more comprehensible, embodiments and accompanying figures are described in detail below.

BRIEF DESCRIPTION OF THE DRAWINGS

The accompanying drawings are incorporated in and constitute a part of this specification. The drawings illustrate exemplary embodiments and, together with their description, serve to explain the principles of the disclosure.

DETAILED DESCRIPTION OF DISCLOSED EMBODIMENTS

A surface topography optical measuring system of the disclosure is adapted to measure surface topography of an object. Specifically, the surface topography optical measuring system of the disclosure is adapted to measure the depth of a concave structure or the height of a convex structure of an object when the structures are located at distances larger than either or both the FOV (Field of View) and working range of an individual image capture module, by obtaining one or more height differences within the FOV and working range of each individual image capture module. For example, the surface topography optical measuring system of the disclosure is adapted to measure the depth of a blind hole when the blind hole diameter can be larger than the FOV of an individual image capture module, or when the depth of the blind hole is larger than the working range of a single image capture module, and similarly for the height of a pin, or height differences of other structures. The embodiments and the figures described below take the blind hole as an example for the convenience of explanation, but the structure of the object to be measured is not limited thereto.

Figure 1A:
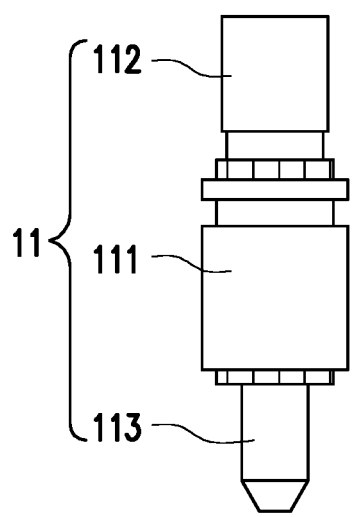
FIG. 1A is a schematic view of an image capture module of a surface topography optical measuring system according to an embodiment of the disclosure.
Figure 1B:
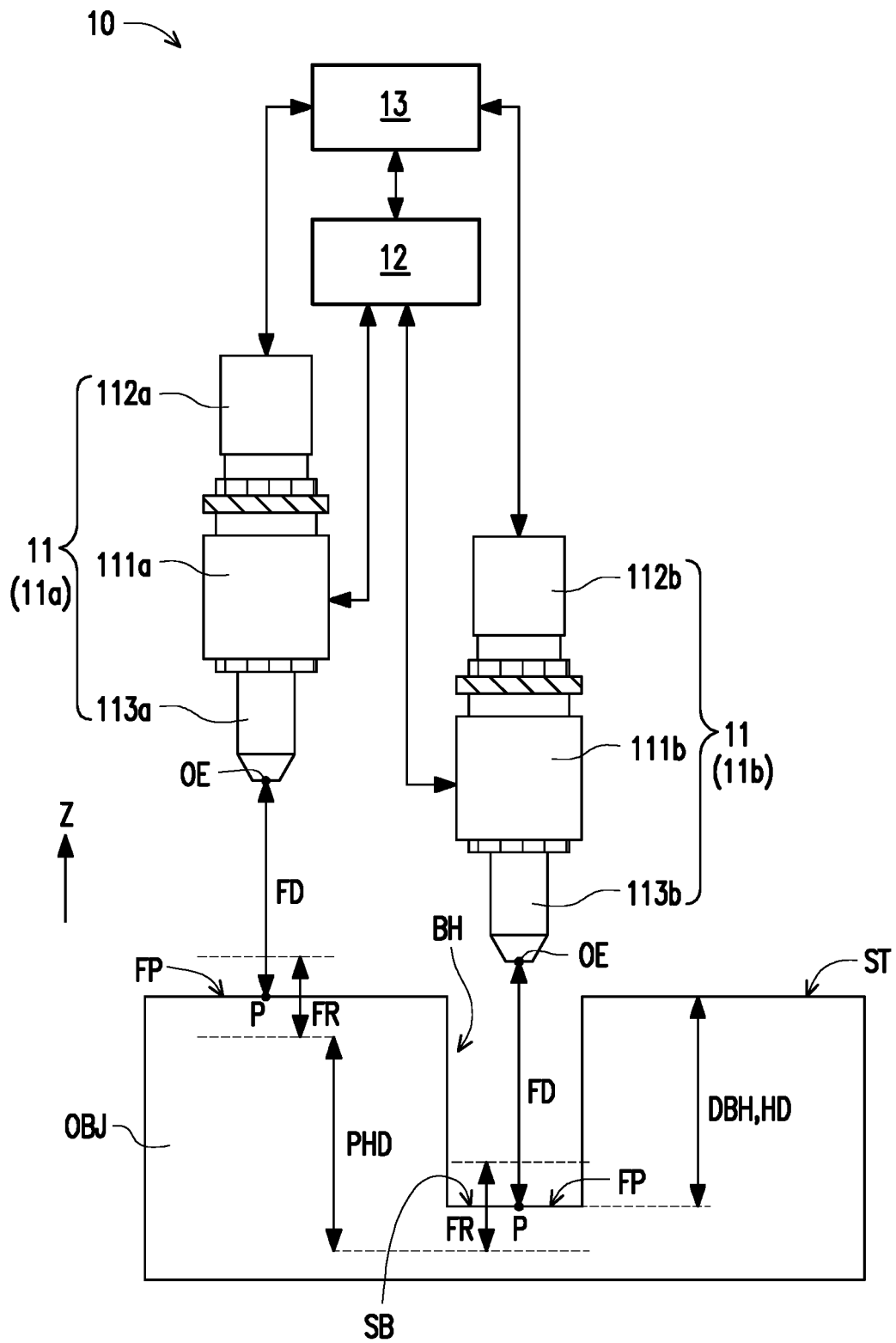
FIG. 1B is a schematic view of a surface topography optical measuring system according to an embodiment of the disclosure.

FIG. 1A is a schematic view of an image capture module used in a surface topography optical measuring system according to an embodiment (e.g. a first embodiment of the image capture module) of the disclosure shown in FIG. 1B. Referring to FIG. 1A, the image capture module 11 includes an electronically controlled focal length tunable lens 111 and an image sensor 112, wherein the image sensor 112 is disposed on a transmission path of a light beam (not shown) from a surface to inspect to the electronically controlled focal length tunable lens 111. The focal length of the electronically controlled focal length tunable lens 111 is controlled by changing the value of an electrical parameter (e.g. a voltage or a current) applied to the electronically controlled focal length tunable lens 111. For example, the electronically controlled focal length tunable lens 111 includes a liquid lens or a liquid crystal lens, and the image sensor 112 includes a charge-coupled device (CCD) or a complementary metal-oxide semiconductor (CMOS), but the disclosure is not limited thereto.

In the embodiment, each of the plurality of image capture modules 11 further includes an optical assembly 113, wherein the electronically controlled focal length tunable lens 111 may be disposed between the optical assembly 113 and the image sensor 112. The optical assembly 113 may include at least one lens element, a filter or other optical elements. The tunable lens 111, the optical assembly 113 and the image sensor 112 are disposed so that the assembly 11 presents an object-side, image-side or bi-telecentric property. Referring to FIG. 1B, a surface topography optical measuring system 10 of the first embodiment of the disclosure includes a plurality of image capture modules 11. FIG. 1B schematically illustrates a first image capture module 11a and a second image capture module 11b, a control module 12 and a computation module 13. The first image capture module 11a includes an electronically controlled focal length tunable lens 111a, an image sensor 112a and an optical assembly 113a. The second image capture module 11b includes an electronically controlled focal length tunable lens 111b, an image sensor 112b and an optical assembly 113b. The elements of the first and second image capture modules may have identical or different specifications. It should be noted that the surface topography optical measuring system 10 may comprise more than two image capture modules 11 according to actual measurement requirements and is not limited to the setup shown in FIG. 1B.

Each of the plurality of image capture modules 11 is characterized by a focusing range FR and a maximum focus distance (MFD). The maximum focus distance is the longest distance, along the optical axis of the image capture module 11, from the frontmost element (e.g. the output end OE) of the optical assembly 113 to a point P on a plane of focus FP on a surface of the object OBJ, so that point P is in focus. The focusing range FR corresponds to the difference in height between the MFD and the shortest distance at which an image capture module 11 can focus. The focus distance FD is the distance at which an image capture module 11 is focused, given a current control state of the tunable lens 111. The focus distance FD of each of the plurality of image capture modules 11 is related to the optical assembly 113 and the electronically controlled focal length tunable lens 111. Specifically, depending on the optical design, the focus distance FD can increase as the focal length of the electronically controlled focal length tunable lens 111 increases, and the focus distance FD can decrease as the focal length of the electronically controlled focal length tunable lens 111 decreases. A different optical design can lead to the opposite variation. In the embodiment, locations of the plurality of image capture modules 11 are fixed when capturing images within focusing ranges FR of the plurality of image capture modules 11. With reference to a relationship between focus distance FD and an electrical parameter shown in FIG. 4, the maximum focus distance is the focus distance when the electrical parameter (e.g. a voltage or a current) applied to the electronically controlled focal length tunable lens 111 is minimal (i.e. when the electronically controlled focal length tunable lens 111 is in an idle state), while the minimum focus distance is the focus distance when the electrical parameter applied to the electronically controlled focal length tunable lens 111 is maximum. Depending on the optical design of the image capture module 11, an opposite variation may take place.

The maximum focus distance MFD and the focusing range FR of each of the plurality of image capture modules 11 depends on the configuration of each of the plurality of image capture modules 11, and the configuration of each of the plurality of image capture modules 11 may be adapted to actual requirements. FIG. 2A to FIG. 2F respectively are schematic views of image capture modules that can be used in embodiments of the disclosure. In FIG. 2A to FIG. 2F, the same elements are indicated by the same reference number and will not be repeated hereinafter.

Figure 2A:
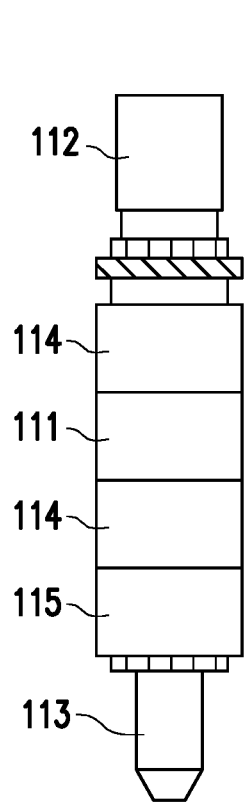
FIG. 2A to FIG. 2F respectively are schematic views of image capture modules that can be used in embodiments of the disclosure.

In FIG. 2A, the image capture module 11A of a second embodiment of the disclosure includes an electronically controlled focal length tunable lens 111, an image sensor 112, an optical assembly 113 (e.g. an infinite conjugate objective lens), two relay lenses 114, and a tube lens 115, wherein the electronically controlled focal length tunable lens 111 is disposed between the two relay lenses 114, and the tube lens 115 is disposed between the optical assembly 113 and the lower relay lenses 114.

Figure 2B:
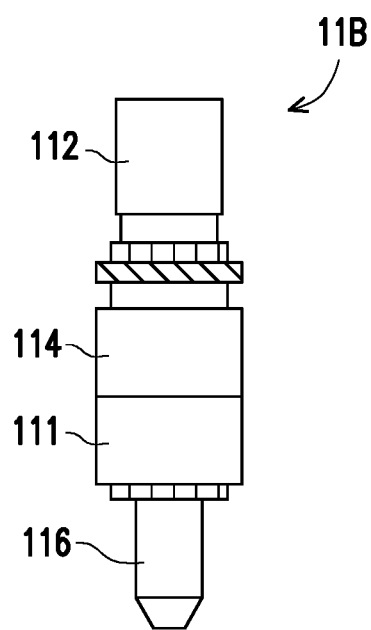

In FIG. 2B, the image capture module 11B of a third embodiment of the disclosure includes an electronically controlled focal length tunable lens 111, an image sensor 112, a relay lens 114 and a finite conjugate objective lens 116, wherein the relay lens 114 is disposed between the electronically controlled focal length tunable lens 111 and the image sensor 112, and the electronically controlled focal length tunable lens 111 is disposed between the finite conjugate objective lens 116 and the relay lens 114.

Figure 2C:
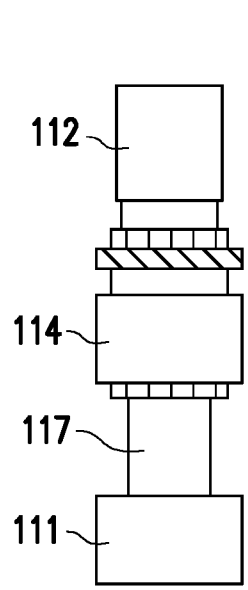

In FIG. 2C, the image capture module 11C of a fourth embodiment of the disclosure includes an electronically controlled focal length tunable lens 111, an image sensor 112, a relay lens 114 and an objective lens 117, wherein the relay lens 114 is disposed between the electronically controlled focal length tunable lens 111 and the image sensor 112, and the objective lens 117 is disposed between the electronically controlled focal length tunable lens 111 and the relay lens 114.

Figure 2D:
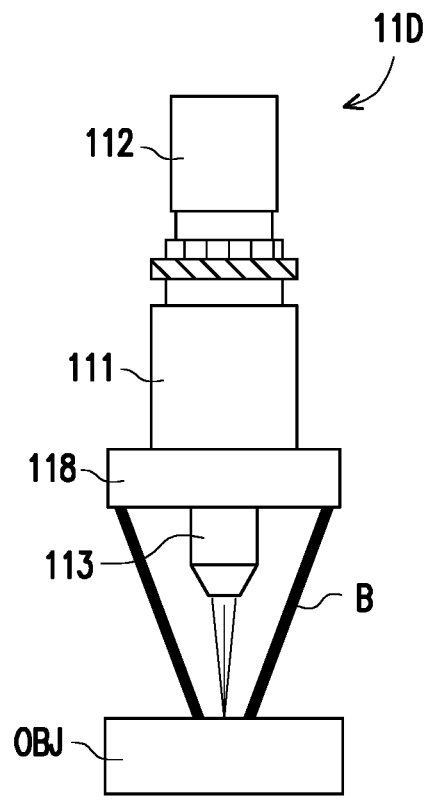

In FIG. 2D, the image capture module 11D of a fifth embodiment of the disclosure includes a ring light source 118 so as to provide a light beam B for illuminating the object OBJ. The ring light source 118 may include at least one light emitting element. For example, the ring light source 118 includes at least one laser diode, at least one light emitting diode, or a combination thereof. It should be noted that the ring light source 118 can be used in any image capture module with other optical designs of the disclosure. In other words, the configuration of the image capture module that includes the ring light source 118 should not be limited to FIG. 2D.

Figure 2E:
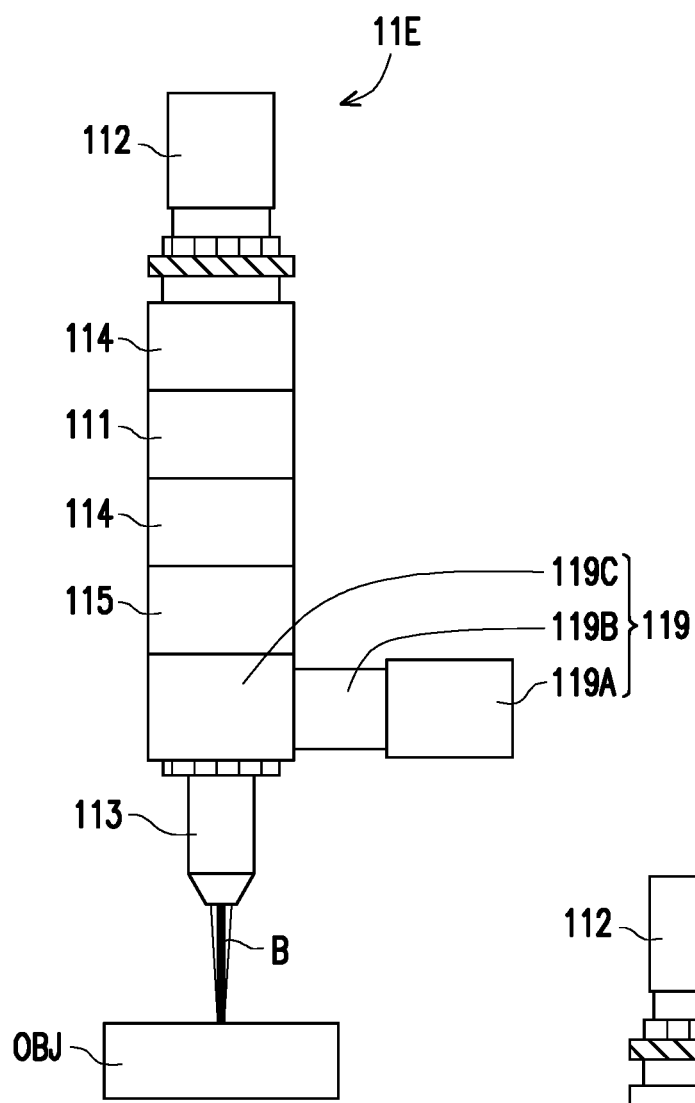

In FIG. 2E, the image capture module 11E of a sixth embodiment of the disclosure is similar to the image capture module 11A in FIG. 2A, and the main difference therebetween is that the image capture module 11E further includes a coaxial light source 119 disposed between the optical assembly 113 (e.g. the infinite conjugate objective lens) and the tube lens 115.

Specifically, the coaxial light source 119 includes a light source 119A, a collimating assembly 119B, and a beam splitter 119C. The light source 119A includes at least one laser diode, at least one light emitting diode, or a combination thereof so as to provide a light beam B for illuminating the object OBJ. The collimating assembly 119B is located between the light source 119A and the beam splitter 119C, and the collimating assembly 119B includes at least one optical element to collimate the light beam from the light source 119A and transmit the collimated light beam to the beam splitter 119C. The beam splitter 119C is located on a transmission path of the collimating assembly 119B and located between the optical assembly 113 and the tube lens 115. The light beam from the light source 119A is transmitted to the beam splitter 119C after passing through the collimating assembly 119B. The light beam passing through the collimating assembly 119B and transmitted to the beam splitter 119C is then transmitted to the optical assembly 113 after reflected by the beam splitter 119C. The light beam reflected by the beam splitter 119C and transmitted to the optical assembly 113 is then transmitted to the object OBJ after passing through the optical assembly 113. The light beam transmitted to the object OBJ is then reflected by the object OBJ and then received by the image sensor 112 after sequentially passing through the optical assembly 113, the beam splitter 119C, the tube lens 115, the relay lens 114 that is closer to the object OBJ, the electronically controlled focal length tunable lens 111, and the relay lens 114 that is away from the object OBJ.

Figure 2F:
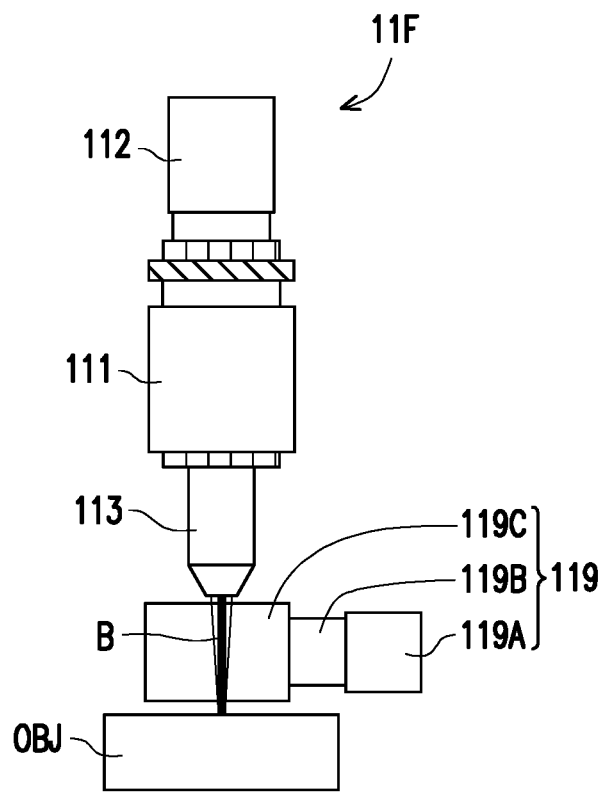

It should be noted that the coaxial light source 119 can be used in any image capture module with other optical designs of the disclosure. In other words, the configuration of the image capture module that includes the coaxial light source 119 should not be limited to FIG. 2E. For example, at least one of the plurality of image capture modules 11 in FIG. 1B can further include the coaxial light source 119, as shown in FIG. 2F. In FIG. 2F, the image capture module 11F of a seventh embodiment of the disclosure is similar to the image capture module 11F in FIG. 2F, and the main difference therebetween is that the image capture module 11F further includes the coaxial light source 119 disposed between the object OBJ and the optical assembly 113. The elements in the coaxial light source 119 are similar to those described in FIG. 2E.

It is noted that one or more of the plurality of image capture modules 11 in the surface topography optical measuring system 10 in FIG. 1B may be replaced by the image capture module 11A in FIG. 2A, the image capture module 11B in FIG. 2B, the image capture module 11C in FIG. 2C, the image capture module 11D in FIG. 2D, the image capture module 11E in FIG. 2E, or the image capture module 11F in FIG. 2F. When the plurality of image capture modules 11 in the surface topography optical measuring system 10 adopt different configurations, the focus distances FD and/or the focusing ranges FR of the plurality of image capture modules 11 need not be the same. In addition, the image sensor 112 in FIGS. 1A to 2F can be an area sensor or a line sensor.

Referring back to FIG. 1B, the control module 12 is coupled to the plurality of image capture modules 11 to independently control the plurality of image capture modules 11. For example, the control module 12 may control each of the plurality of image capture modules 11 to capture images and control the focal length of each electronically controlled focal length tunable lens 111 by varying the input electrical parameter.

The control module 12 may include one or more controllers to independently control the plurality of image capture modules 11. In one embodiment, the control module 12 may be built in one or more of the plurality of image capture modules 11 or built in a mobile device, a gateway, or a cloud system, etc.

Figure 4:
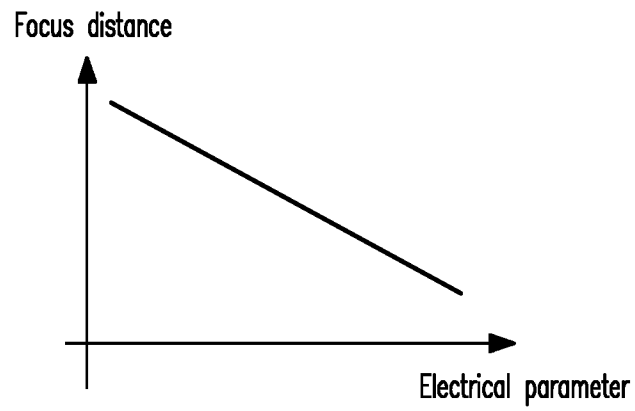
FIG. 4 and FIG. 5 respectively are schematic views showing steps for calibration of the surface topography optical measuring system.

The computation module 13 is coupled to the control module 12 and the image sensor 112 of each of the plurality of image capture modules 11, wherein the computation module 13 performs calibration of the surface topography optical measuring system 10 and assesses in-focused pixels in the captured images to measure a height difference between a lowest and a highest surfaces of the object OBJ or between any surfaces of interest of the object OBJ. Specifically, the calibration of the surface topography optical measuring system 10 may include obtaining a relationship between the electrical parameter and the focus distance of each of the plurality of image capture modules 11 and performing a calibration on the plurality of image capture modules 11 so that a predetermined height difference PHD is obtained between planes of focus FP of the plurality of image capture modules 11 when the electronically controlled focal length tunable lens 111 of each of the plurality of image capture modules 11 is in an idle state (i.e. when the electrical parameter applied to the electronically controlled focal length tunable lens 111 is minimum as shown in FIG. 4). In one embodiment, the computation module 13 may be built in one or more of the plurality of image capture modules 11 or built in a mobile device, a gateway, or a cloud system, etc.

In the embodiment, the surface topography optical measuring system 10 is adapted to measure the surface topography of the object OBJ having a blind hole BH. Specifically, the surface topography optical measuring system 10 is adapted to obtain a depth DBH of the blind hole BH. The plurality of image capture modules 11 are respectively disposed over a lowest and a highest surfaces of the object OBJ so as to capture images of said lowest and highest surfaces of the object OBJ. As shown in FIG. 1B, the first image capture module 11A is disposed over a top surface ST of the blind hole BH to capture images of the top surface ST of the blind hole BH, while the second image capture module 11B is disposed over a bottom surface SB of the blind hole BH to capture images of the bottom surface SB of the blind hole BH. The number of image capture modules 11 can be adapted to match the geometry of the object OBJ and the measurement requirements. For example, in one embodiment, more than one image capture modules 11 can be used to capture images of the top surface ST of the blind hole BH.

Figure 3:
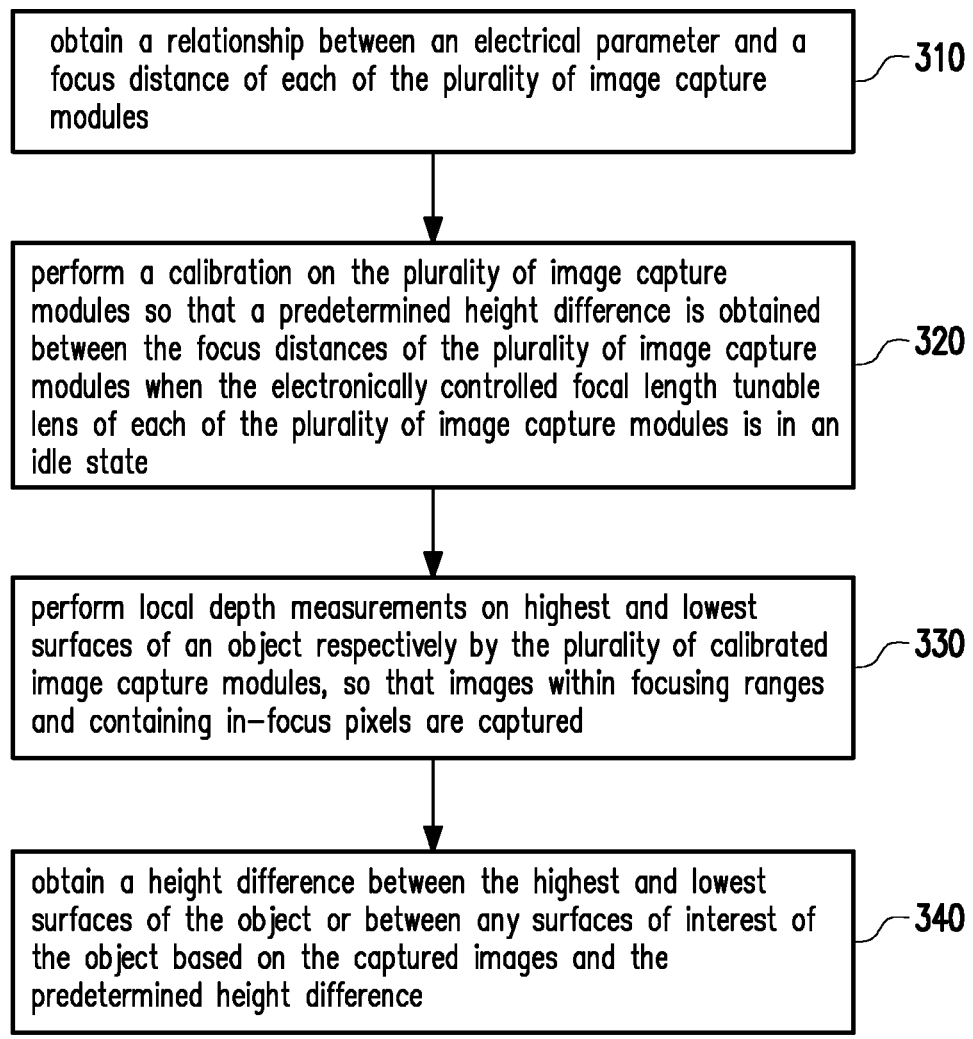
FIG. 3 is a flow chart of a surface topography optical measuring method according to an embodiment of the disclosure.
Figure 5:
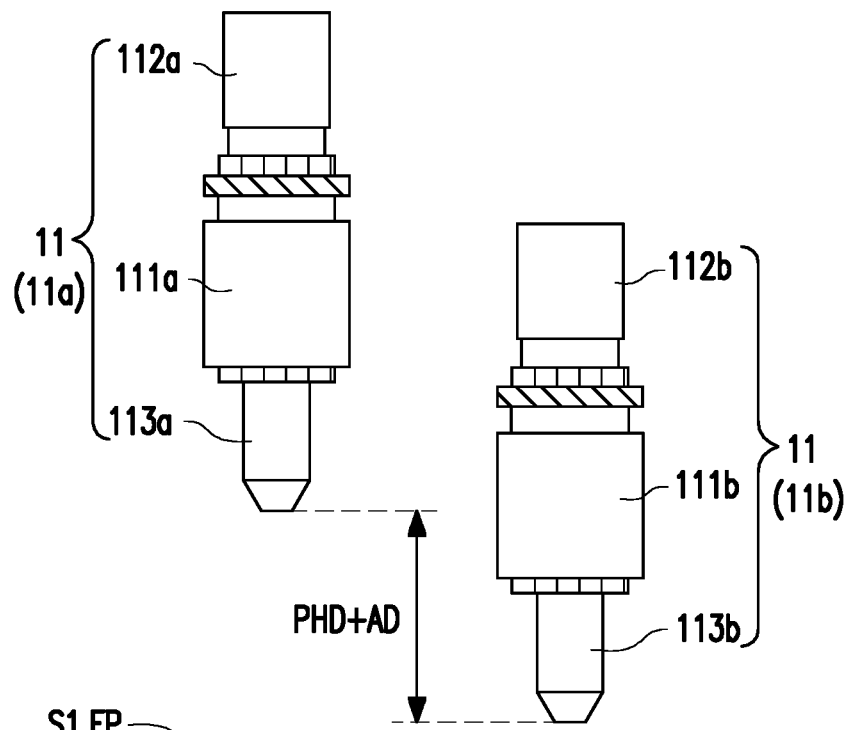
Figure 5:
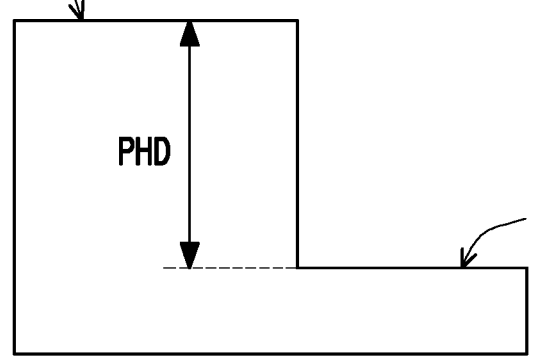

A surface topography optical measuring method using the plurality of image capture modules is now illustrated with reference to FIG. 3 to FIG. 6D. FIG. 3 is a flow chart of a surface topography optical measuring method according to an embodiment of the disclosure. FIG. 4 and FIG. 5 respectively are schematic views showing steps for calibration of the surface topography optical measuring system. FIG. 6A to FIG. 6F respectively are images captured by image capture modules of a surface topography optical measuring system according to an exemplary implementation of the method.

FIG. 1B and FIG. 3 to FIG. 6F, in step 310, illustrate how to establish a relationship between an electrical parameter (e.g. a voltage or a current) and a focus distance FD of each of the plurality of image capture modules 11. Specifically, the focus distance FD of each of the plurality of image capture modules 11 changes with variation of the electrical parameter applied to the electronically controlled focal length tunable lens 111. Therefore, the focus distance variation of two images captured by the same image capture module 11 can be obtained by the following steps. First, in step 310 of FIG. 3, obtain a relationship such as illustrated on FIG. 4 between the values of the electrical parameters applied to the plurality of electronically controlled focal length tunable lenses of FIG. 1B (111a and 111b) and the focus distances FD of each of the plurality of electronically controlled focal length tunable lenses of FIG. 1B. This relationship can be obtained by capturing images of an object having surfaces at known heights, then obtaining the in-focused pixels in each of the captured image and finally relating said images with in-focused pixels to the electrical parameters at which said images were captured. In the subsequent calculation process, the focus distance variation between in-focus pixels in different images captured by the same image capture module 11 can be derived from the electrical parameter variation corresponding to the captured images.

In step 320, perform a calibration on the plurality of image capture modules 11 so that a predetermined height difference PHD is obtained between the planes of focus FP of the plurality of image capture modules 11 when the electronically controlled focal length tunable lens (111a or 111b) of each of the plurality of image capture modules 11 is in an idle state. Specifically, referring to FIG. 5, perform the calibration on the plurality of image capture modules 11 includes the following steps. First, capture images of the high surface S1 of a calibration gage 500 using the first image capture module 11a and images of the low surface S2 of the calibration gage 500 using the second image capture module 11b when the electronically controlled focal length tunable lens (111a or 111b) of each of the plurality of image capture modules 11 is in the idle state, wherein the high and low surfaces of the calibration gage 500 have an accurately known predetermined height difference PHD. Then, adjusting the respective distance between each of the plurality of image capture modules 11 so that the planes of focus FP of each of the plurality of image capture modules 11 are respectively on the high and low surfaces of the calibration gage 500 when the electronically controlled focal length tunable lens (111a or 111b) of each of the plurality of image capture modules 11 is in the idle state, resulting in that the height difference between the image capture modules 11 as seen on FIG. 5 is equal to PHD+AD, where AD is an adjusting distance. When the image capture modules 11 are rigorously identical, then AD=0. However, since the focus distance of each image capture module 11 when each image capture module 11 is in an idle state may not be equal, either due to different optical characteristics, or due to minute manufacturing difference, or due to minute tunable lens optical characteristic when the tunable lens is at rest, the adjusting distance AD may be positive or negative.

An additional adjustment can be performed by varying the electrical parameter applied to any of the electronically controlled focal length tunable lens so that their respective planes of focus FP be accurately located on the high and low surfaces of the calibration gage 500. After step 320, the planes of focus (PoF) of the image capture modules 11 are respectively on the high and low surfaces of the calibration gage 500 when the electronically controlled focal length tunable lens (111a and 111b) of each of the plurality of image capture modules 11 is in the idle state The predetermined height difference PHD between the high and low surfaces of the calibration gage 500 in FIG. 5 is selected based on the expected design values of the depth DBH of the blind hole BH shown in FIG. 1B. In other words, the variation of the focus distances FD of the calibrated plurality of image capture modules 11 is within the range of the actual depth DBH of the blind hole BH. Accordingly, when the calibration gage 500 is replaced by the object OBJ, the actual depth DBH of the blind hole BH can be measured by local variation of the focus distance FD of each of the plurality of image capture modules 11 through the variation of the input electrical parameter, and the focusing range FR of each of the plurality of image capture modules 11 can be smaller than the height difference HD between a lowest and a highest surfaces of the object OBJ (i.e. the depth DBH of the blind hole BH). Thus, the focusing range FR of each of the plurality of image capture modules 11 needs not to cover the whole depth DBH of the blind hole BH, so that images need only to be captured over the focusing range FR of each image capture module rather than over the whole depth DBH, thereby shortening the measurement time. This also enables to measure heights of objects with dimensions larger than the focusing range FR of an individual image capture module 11. The focusing range FR of each of the plurality of image capture modules 11 may be changed according to actual requirements, and the disclosure is not intended to limit the focusing range FR of each of the plurality of image capture modules 11.

In step 330, local depth measurements on a highest and a lowest surfaces (top surface ST and bottom surface SB on FIG. 1B) of an object OBJ by the respective calibrated image capture modules 11 are performed, so that images within focusing range FR of the plurality of calibrated image capture modules 11 and containing in-focus pixels are captured. In the embodiment, as shown in FIG. 1B, the focusing ranges FR of each of the plurality of image capture modules 11 may be different.

FIG. 6A to FIG. 6F are schematic representations of images captured by a plurality of calibrated image capture modules according to an exemplary embodiment.

Figure 6A:
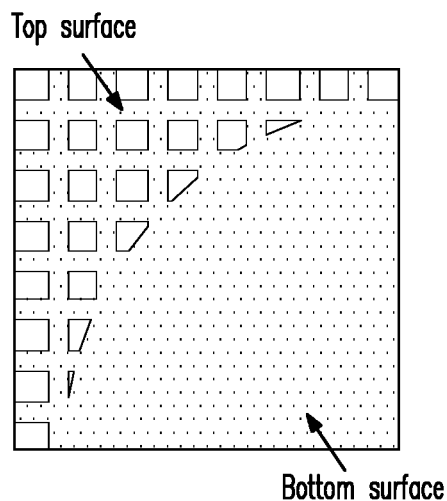
FIG. 6A to FIG. 6F respectively are images captured by image capture modules of a surface topography optical measuring system according to an exemplary application of the disclosure.
Figure 6B:
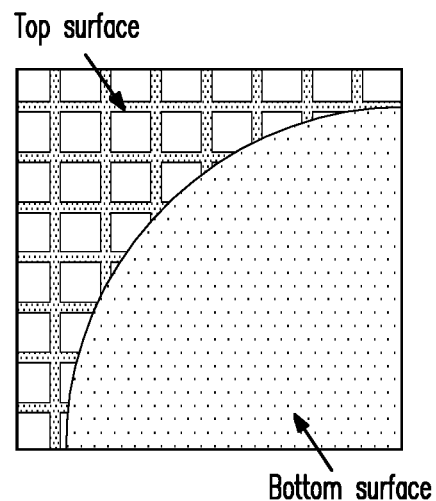
Figure 6C:
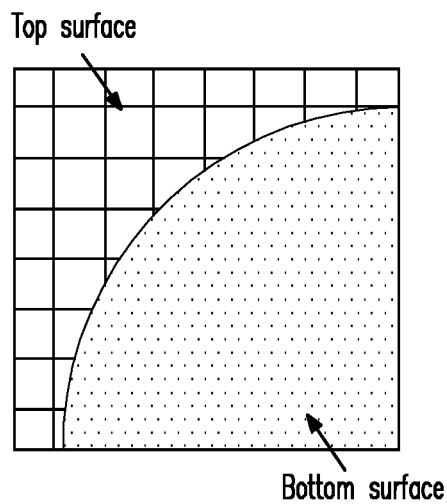
Figure 6D:
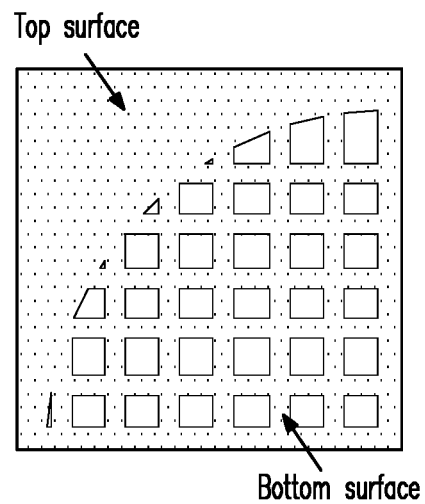
Figure 6E:
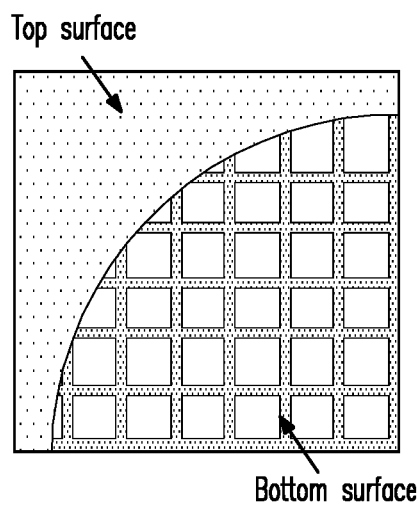
Figure 6F:
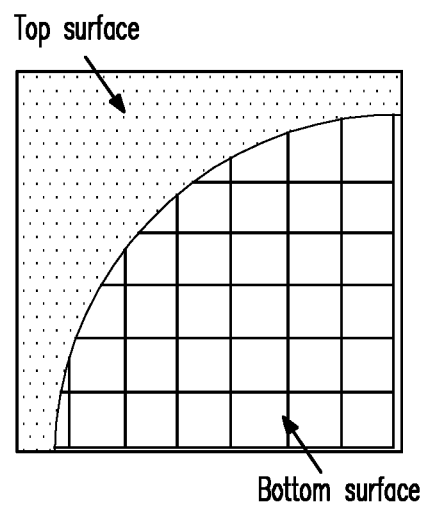

FIGS. 6A to 6C show the top of a blind hole as seen by the first image capture module 11a of FIG. 1B and FIGS. 6D to 6F show the bottom of a blind hole as seen by the second image capture module 11b of FIG. 1B. The first image capture module 11a is set so that the top surface of the blind hole is within focusing range of the first image capture module 11a. FIGS. 6A to 6C show an increasing degree of focus of the top surface with FIG. 6C showing the top surface in focus, while the bottom surface is totally out-of-focus. FIGS. 6D to 6F show the bottom of a blind hole as seen by the second image capture module 11b. The second image capture module 11b is set so that the bottom surface of the blind hole is within focusing range of the second image capture module 11b. FIGS. 6D to 6F show an increasing degree of focus of the bottom surface with FIG. 6F showing the bottom surface in focus, while the top surface is totally out-of-focus. Note that the whole depth of the blind hole is outside the focusing range of any of the image capture modules 11.

In step 340 of FIG. 3, obtain a height difference HD between a lowest and a highest surfaces of the object OBJ or between any surfaces of interest of the object based on the captured images and the predetermined height difference PHD. Specifically, obtaining the height difference HD between a lowest and a highest surfaces of the object OBJ may include steps as follow. First, select the in-focus pixels in the captured images. Then, match each of the in-focus pixels with a corresponding focus distance FD by using the relationship between an electrical parameter and a focusing distance obtained in step 310 and as shown in FIG. 4. Then, the height difference HD between a lowest and a highest surfaces of the object OBJ or between any surfaces of interest of the object OBJ can be obtained based on the predetermined height difference plus the adjusting distance (PHD+AD) between the plurality of image capture modules 11 and the focus distance variation (from idle state of the electronically controlled focal length tunable lens) derived from the electrical parameter variation of the electronically controlled focal length tunable lens 111 in each of the plurality of image capture modules 11. For example, if the focus distance variation corresponding to the in-focus pixels in the image captured at the bottom surface SB by the second image capture module 11b is X, and the focus distance variation corresponding to the in-focus pixels in the image captured at the top surface ST by the first image capture module 11a is Y, then the height difference HD between a lowest and a highest surfaces of the object OBJ (i.e. the depth DBH of the blind hole BH) equals to (PHD+AD+|X−Y|).

Figure 7:
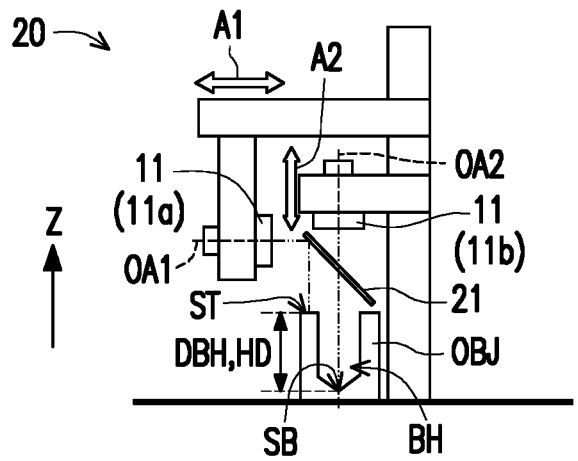
FIG. 7 to FIG. 9 respectively are schematic views of surface topography optical measuring systems according to other embodiments of the disclosure.
Figure 8:
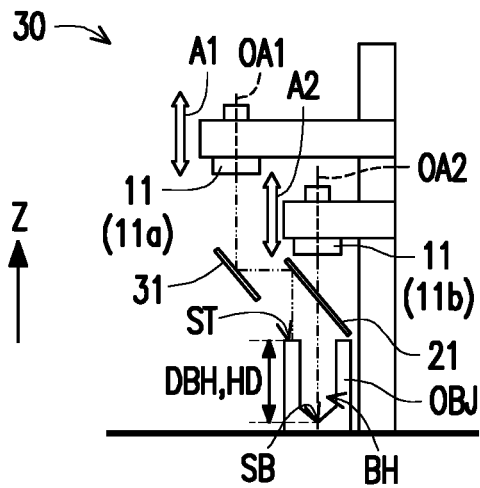
Figure 9:
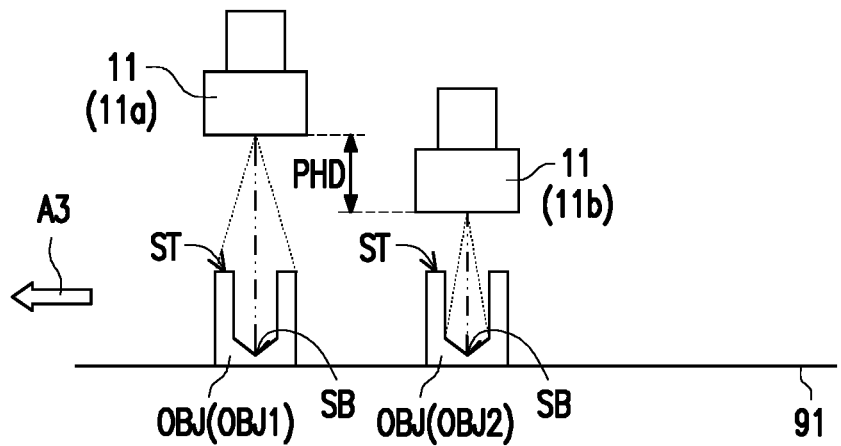

FIG. 7 to FIG. 9 respectively are schematic views of a surface topography optical measuring systems according to other embodiments of the disclosure. In FIG. 7 to FIG. 9, the same elements are indicated by the same reference number and will not be repeated hereinafter.

Referring to FIG. 7, the surface topography optical measuring system 20 of a second embodiment of the disclosure includes a partially reflective optical element 21 disposed between the object OBJ and each of the plurality of image capture modules 11. A central region of the partially reflective optical element 21 is designed to allow a light beam from the bottom surface SB of the blind hole BH to pass through and be imaged by the first image capture module 11a. A peripheral region of the partially reflective optical element 21 is designed to reflect a light beam from the top surface ST of the blind hole BH and be imaged by the second image capture module 11b (if a light source is included in the second image capture module 11b). For example, the partially reflective optical element 21 can be a specially made mirror with a transmissive central region and a reflective peripheral region. Alternatively, the partially reflective optical element 21 can be a beam splitter. In the case where the first image capture module 11a and the second image capture module 11b respectively include light sources with different wavelengths (e.g. a visible light source and an IR light source), the partially reflective optical element 21 can be a hot mirror or a cold mirror, but the disclosure is not limited thereto.

In the configuration of FIG. 7, during the calibration of the plurality of image capture modules 11, locations of the first image capture module 11a and the second image capture module 11b can be adjusted by moving the first image capture module 11a and the second image capture module 11b along directions respectively indicated by arrows A1 and A2 shown in FIG. 7.

Referring to FIG. 8, in the surface topography optical measuring system 30 of a third embodiment of the disclosure, the first image capture module 11a and the second image capture module 11b both face the object OBJ so that the optical axis OA1 of the first image capture module 11a is parallel to the optical axis OA2 of the second image capture module 11b. In addition, the surface topography optical measuring system 30 further includes a reflector 31 disposed between the partially reflective optical element 21 and one of the plurality of image capture modules 11 (e.g. the first image capture module 11a). The reflector 31 is located outside a light transmission path between the object OBJ and the other (for example, the second image capture module 11b) of the plurality of image capture modules. In other words, the reflector 31 is not located between the partially reflective optical element 21 and the second image capture module 11b, and the reflector 31 is not located between the partially reflective optical element 21 and the object OBJ, so that the second image capture module 11b is able to capture a light beam (not shown) from the bottom surface SB of the object OBJ. The light beam (not shown) from the top surface ST of the blind hole BH is transmitted to the first image capture module 11a after sequentially reflections by the partially reflective optical element 21 and the reflector 31. The reflector 31 may include a mirror or a plate coated with a reflecting layer.

Referring to FIG. 9, in the surface topography optical measuring system of a fourth embodiment of the disclosure, a plurality of objects OBJ (e.g. a first object OBJ1 and a second object OBJ2) are disposed on a conveyor belt 91 which translates the plurality of objects OBJ along a direction indicated by an arrow A3. The first image capture module 11a is used to capture images of the top surface ST in each of the plurality of objects OBJ, and the second image capture module 11b is used to capture images of the bottom surface SB in each of the plurality of objects OBJ.

For example, as the plurality of objects OBJ are being conveyed and object OBJ1 passes under an image capture module (e.g. 11b), the image capture module (e.g. 11b) captures images of the bottom surface SB of object OBJ1. As the plurality of objects OBJ move further along the conveyor belt, objects OBJ1 and OBJ2 are located under image capture modules (e.g. 11a and 11b) respectively; the image capture module (e.g. 11a) located over the object OBJ1 captures images of the top surface ST of the object OBJ1 and the image capture module (e.g. 11b) located over the object OBJ2 captures images of the bottom surface SB of the object OBJ2 simultaneously. When the object OBJ2 passes under the image capture module (e.g. 11a) used to capture images of the top surface ST in each of the plurality of objects OBJ, the image capture module (e.g. 11a) captures images of the top surface ST of object OBJ2.

It is noted that FIG. 9 schematically shows two objects OBJ, but the number of objects OBJ is not limited thereto.

In summary, in the embodiments of the disclosure, 2D images of the surfaces of an object under inspection are obtained. In addition, the images of a highest and a lowest surfaces (or any surfaces of interest in-between) of the object are captured by the plurality of image capture modules simultaneously. Therefore, the surface topography optical measuring system and the surface topography optical measuring method of the disclosure are able to obtain the surface topography of the object at a high speed. Moreover, the surface topography optical measuring system and the surface topography optical measuring method of the disclosure can be adapted to obtain depth measurements of concave or convex structure that are larger in depth or lateral dimensions than the specifications of a single traditional surface topography optical measuring system. In one embodiment, more than one height differences in the object can be measured by increasing the number of image capture modules. The electronically controlled focal length tunable lens and the optical assembly of the image capture module in embodiments of the disclosure form an image-side telecentric lens, an object-side telecentric lens or a bi-telecentric lens.

It will be apparent to those skilled in the art that various modifications and variations can be made to the structure of the disclosed embodiments without departing from the scope or spirit of the disclosure. In view of the foregoing, it is intended that the disclosure covers modifications and variations of this disclosure provided they fall within the scope of the following claims and their equivalents.

What is claimed is:

1. A surface topography optical measuring system, comprising:
    a plurality of image capture modules, each of the plurality of image capture modules comprising an electronically controlled focal length tunable lens, an optical assembly and an image sensor, wherein the plurality of image capture modules respectively capture images at different heights between a lowest and a highest surfaces of an object;
    one or more controllers, coupled to the plurality of image capture modules to independently control the plurality of image capture modules; and
    one or more computing logic, coupled to the one or more controllers and the image sensor of each of the plurality of image capture modules, wherein the one or more computing logic performs calibration of the surface topography optical measuring system and assesses in-focused pixels in the captured images to measure a height difference between a highest and a lowest surfaces of the object or between any surfaces of interest of the object.

2. The surface topography optical measuring system as recited in claim 1, wherein each of the plurality of image capture modules has a focusing range in a thickness direction of the object, and the focusing range of each of the plurality of image capture modules is smaller than the height difference between a lowest and a highest surfaces of the object.

3. The surface topography optical measuring system as recited in claim 1, wherein a predetermined height difference is obtained between focus distances of the plurality of image capture modules when the electronically controlled focal length tunable lens of each of the plurality of image capture modules is in an idle state.

4. The surface topography optical measuring system as recited in claim 1, wherein at least one of the plurality of image capture modules comprises an infinite conjugate objective lens or a finite conjugate objective lens.

5. The surface topography optical measuring system as recited in claim 1, wherein the electronically controlled focal length tunable lens and the optical assembly of the image capture module form an image-side telecentric lens, an object-side telecentric lens or a bi-telecentric lens.

6. The surface topography optical measuring system as recited in claim 1, wherein at least one of the plurality of image capture modules comprises a coaxial light source or a ring light source.

7. The surface topography optical measuring system as recited in claim 6, wherein the coaxial light source or the ring light source includes at least one laser diode, or at least one light emitting diode, or a combination thereof.

8. The surface topography optical measuring system as recited in claim 1, wherein the image sensor of each of the plurality of image capture modules is an area sensor or a line sensor.

9. The surface topography optical measuring system as recited in claim 1, further comprising:
    a partially reflective optical element, disposed between the object and each of the plurality of image capture modules.

10. The surface topography optical measuring system as recited in claim 9, further comprising:
    a reflector, disposed between the partially reflective optical element and one of the plurality of image capture modules, wherein the reflector is located outside a light transmission path between the object and the other of the plurality of image capture modules.

11. The surface topography optical measuring system as recited in claim 1, further comprising:
    a conveyor belt, on which objects are disposed.

12. A surface topography optical measuring method, using the surface topography optical measuring system as recited in claim 1, the surface topography optical measuring method comprising steps of:
    obtaining a relationship between an electrical parameter and a focus distance of each of the plurality of image capture modules;
    performing a calibration on the plurality of image capture modules so that a predetermined height difference is obtained between focus distances of the plurality of image capture modules when the electronically controlled focal length tunable lens of each of the plurality of image capture modules is in an idle state;
    performing local depth measurements on a highest surface and a lowest surface of an object respectively by the plurality of calibrated image capture modules, so that images within focusing ranges and containing in-focus pixels are captured; and
    obtaining a height difference between a lowest and a highest surfaces of the object or between any surfaces of interest of the object based on the captured images and the predetermined height difference.

13. The surface topography optical measuring method as recited in claim 12, wherein the electrical parameter is a voltage or a current.

14. The surface topography optical measuring method as recited in claim 12, wherein performing a calibration on the plurality of image capture modules comprises:
    capturing respectively, by the plurality of image capture modules, images of high and low surfaces of a calibration gage when the electronically controlled focal length tunable lens of each of the plurality of image capture modules is in the idle state, wherein a height difference between the high and low surfaces of the calibration gage is accurately known; and adjusting locations of the plurality of image capture modules so that the image captured by each image capture module is in focus.

15. The surface topography optical measuring method as recited in claim 12, wherein obtaining the height difference between the highest and lowest surfaces of the object comprises:

selecting the in-focus pixels in the captured images; and
matching each of the in-focus pixels with a corresponding distance.

\* \* \* \* \*